(12) United States Patent
Kinugasa et al.

(10) Patent No.: US 10,478,642 B2
(45) Date of Patent: Nov. 19, 2019

(54) PARTICLE BEAM TREATMENT APPARATUS

(71) Applicants: KABUSHIKI KAISHA TOSHIBA, Minato-ku (JP); Toshiba Energy Systems & Solutions Corporation, Kawasaki-shi (JP)

(72) Inventors: Kunihiko Kinugasa, Yokohama (JP); Kiyohiko Kitagawa, Yokohama (JP); Hideo Kobayashi, Ota (JP); Shigeru Kasai, Yokohama (JP); Kazutaka Maeta, Yokohama (JP); Yoshifumi Nagamoto, Yokohama (JP)

(73) Assignees: KABUSHIKI KAISHA TOSHIBA, Minato-ku (JP); Toshiba Energy Systems & Solutions Corporation, Kawasaki-shi (JP)

( * ) Notice: Subject to any disclaimer, the term of this patent is extended or adjusted under 35 U.S.C. 154(b) by 0 days.

(21) Appl. No.: 15/988,611

(22) Filed: May 24, 2018

(65) Prior Publication Data

US 2018/0345043 A1      Dec. 6, 2018

(30) Foreign Application Priority Data

May 31, 2017   (JP) ................................. 2017-107399

(51) Int. Cl.
A61N 5/10      (2006.01)

(52) U.S. Cl.
CPC .... A61N 5/1081 (2013.01); *A61N 2005/1087* (2013.01); *A61N 2005/1094* (2013.01)

(58) Field of Classification Search
CPC .......... A61N 5/1081; A61N 2005/1087; A61N 2005/1094

USPC ........................................... 250/492.1, 492.3
See application file for complete search history.

(56) References Cited

U.S. PATENT DOCUMENTS

| | | | |
|---|---|---|---|
| 5,993,373 A | 11/1999 | Nonaka et al. | |
| 2013/0184512 A1 | 7/2013 | Yajima | |
| 2014/0367570 A1 | 12/2014 | Kimba et al. | |
| 2017/0001041 A1* | 1/2017 | Yamashita | A61N 5/1049 |

FOREIGN PATENT DOCUMENTS

| | | |
|---|---|---|
| JP | 11-47287 | 2/1999 |
| JP | 2001-129103 A | 5/2001 |
| JP | 2001-353228 | 12/2001 |
| JP | 2011-156263 | 8/2011 |
| JP | 2017-55958 A | 3/2017 |
| TW | 200603196 A | 1/2006 |
| TW | 201208733 A1 | 3/2012 |

* cited by examiner

*Primary Examiner* — Nicole M Ippolito
(74) *Attorney, Agent, or Firm* — Oblon, McClelland, Maier & Neustadt, L.L.P.

(57) ABSTRACT

A particle beam treatment apparatus includes: a rotating gantry configured to axially rotate in a state where a bed fixed to a stationary system is disposed inside the rotating gantry and an irradiation port of a beam is fixed to a body of the rotating gantry; a tunnel structure configured to have at least a horizontal floor surface and have an internal space in which at least a part of the bed is accommodated; and a rotation supporter configured to cause the tunnel structure to be stationary in the stationary system independently of axis rotation of the rotating gantry by rotationally displacing the tunnel structure with respect to an inner side surface of the rotating gantry.

5 Claims, 5 Drawing Sheets

PARTICLE BEAM TREATMENT APPARATUS

CROSS-REFERENCE TO RELATED APPLICATION

This application claims the benefit of priority of Japanese Patent Application No. 2017-107399, filed May 31, 2017, the entire contents of which are incorporated herein by reference.

BACKGROUND OF THE INVENTION

Field of the Invention

Embodiments described herein generally relate to a particle beam treatment apparatus equipped with a rotating gantry.

Description of the Related Art

A particle beam therapy is widely practiced as treatment of irradiating a particle beam such as a proton beam and a carbon ion beam onto a lesion area (e.g., cancer) of a patient. As one of such particle beam therapies, there is a known technique in which a patient lying on a treatment bed is positioned and irradiated with a particle beam in a treatment room formed inside a large rotation mechanism (hereinafter referred to as a rotating gantry).

Such a particle beam treatment apparatus equipped with a rotating gantry irradiates a particle beam onto a lesion area of a patient from an arbitrary direction by rotating an irradiation port fixed to the rotating gantry and/or displacing the treatment bed in the treatment room.

The treatment room formed inside the rotating gantry is formed with a moving floor which is composed of a horizontal and flat floor surface and the other surface in the form of an arch along the inner circumference of the rotating gantry, regardless of the rotation position of the rotating gantry.

Additionally, the irradiation port penetrate the opening of the moving floor, and the moving floor is caused to fully rotate in synchronization with rotation of the rotating gantry. Further, there is provided a function of adjusting the size of the opening of the moving floor and filling the gap with the penetrating irradiation port, corresponding to the rotational position of the irradiation port. If this gap is large, it becomes difficult for a technician to access the bed and increases the risk of falling of a utensil or the like to the outside of the treatment room, so the above function is provided.

PRIOR ART

Patent Document 1; Japanese Unexamined Patent Application Publication No. 1999-47287
Patent Document 2; Japanese Unexamined Patent Application Publication No. 2001-353228
Patent Document 3; Japanese Unexamined Patent Application Publication No. 2011-156263.

Since the treatment room is formed with the moving floor which maintains the horizontal flat floor surface and the arch surface while rotating a full axial rotation (i.e., ±180°), it is possible to improve workability of a technician in the internal space of the treatment room and to reduce oppressive feeling of a patient lying on the treatment bed.

However, when the treatment room is formed with such a moving floor, the mechanical rigidity of the moving floor is required to a certain degree and thus it is not possible to take a wide space of the treatment room especially in the rotational axis direction. For this reason, improvement in workability of a technician and reduction in oppressive feeling of a patient are insufficient.

As to the function of adjusting the size of the opening of the moving floor, in conventional technology, there is a problem that noise is generated due to rubbing of contact surfaces of a slide coupling mechanism to be adopted and application of this function is restricted.

In view of the above-described problems, it is an object of embodiments of the present invention to provide a particle beam treatment apparatus which has a wide treatment space and is excellent in general versatility and robustness.

DETAILED DESCRIPTION OF THE PREFERRED EMBODIMENTS

First Embodiment

Hereinbelow, embodiments of the present invention will be described with reference to the accompanying drawings.

Figure 1A:
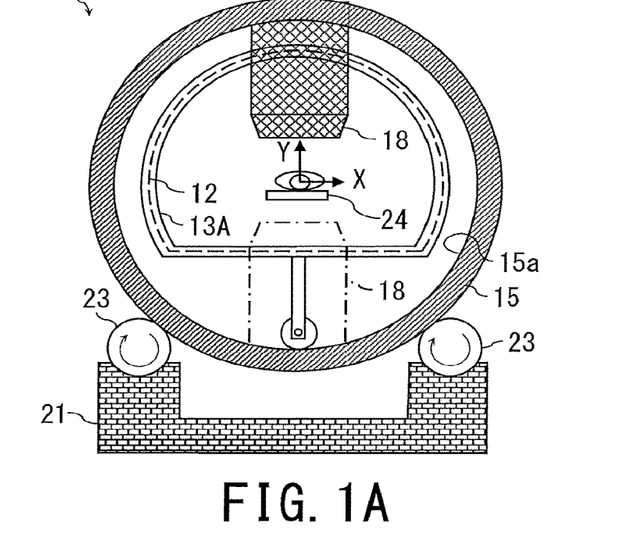
FIG. 1A is an X-Y cross-sectional view of the particle beam treatment apparatus according to the first embodiment of the present invention.
Figure 1B:
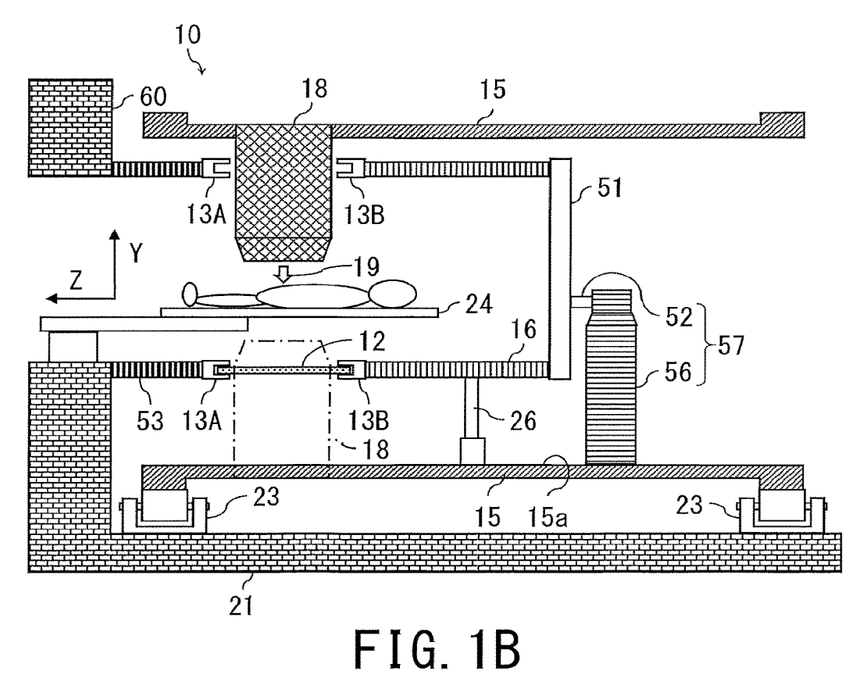
FIG. 1B is an Y-Z cross-sectional view of the particle beam treatment apparatus according to the first embodiment.

FIG. 1A and FIG. 1B are an X-Y cross-sectional view and an Y-Z cross-sectional view of the particle beam treatment apparatus 10 of the first embodiment, respectively.

Figure 2A:
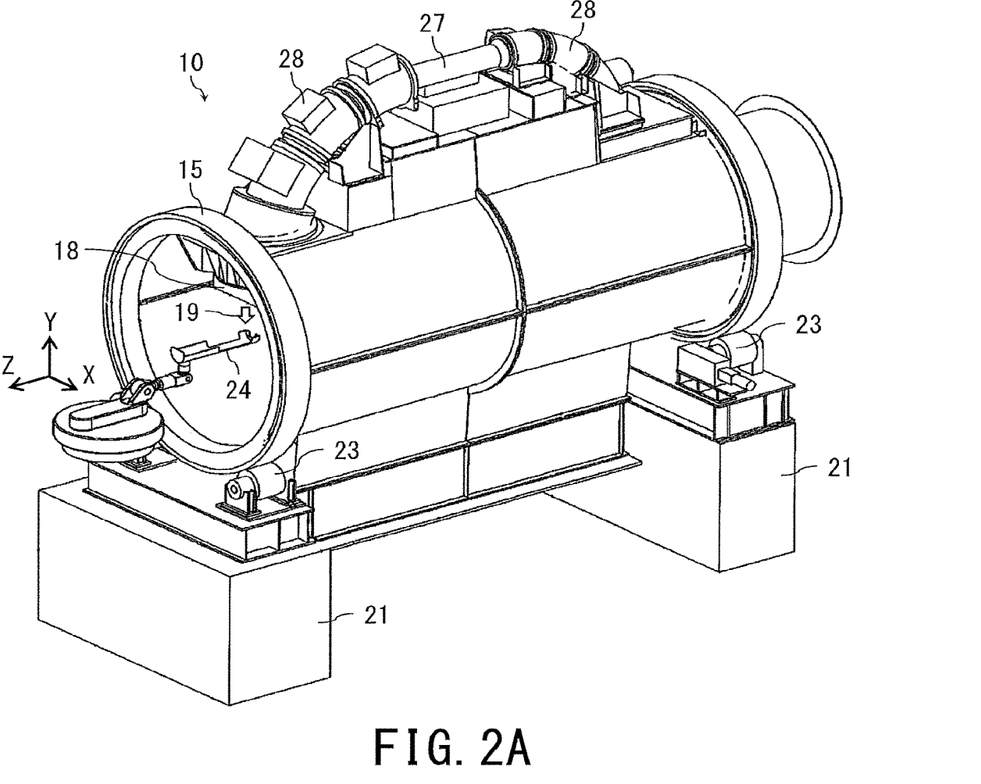
FIG. 2A is a perspective view illustrating the appearance of the particle beam treatment apparatus of each embodiment.

FIG. 2A is a perspective view illustrating the appearance of the particle beam treatment apparatus 10.

As shown in FIG. 1A, FIG. 1B, and FIG. 2A, the particle beam treatment apparatus 10 includes a rotating gantry 15, a tunnel structure 16, and a rotation supporter 57. The rotating gantry 15 axially rotates in a state where a bed 24 fixed to a stationary system is disposed inside the rotating gantry 15 and an irradiation port 18 of a beam 19 is fixed to the body of the rotating gantry 15. The tunnel structure 16 has a horizontal floor surface and an arch-shaped ceiling, and is provided with an internal space in which at least a part of the bed 24 is accommodated. The rotation supporter 57 causes the tunnel structure 16 to be stationary in the stationary system regardless of the axis rotation of the rotating gantry 15, by rotationally displacing the tunnel structure 16 with respect to an inner side surface 15a of the rotating gantry 15.

The particle beam treatment apparatus 10 further includes a moving floor 12 which is formed by joining multiple plates 11 (FIG. 2B) in the circumferential direction to each other such that the moving floor 12 is bendable as a whole and the internal space from the tunnel structure 16 becomes continuous. The moving floor 12 rotates about the Z-axis (i.e., the central axis of the rotating gantry 15) together with the rotating gantry 15 in a state where the irradiation port 18 penetrates the moving floor 12.

As shown in FIG. 2A, the rotating gantry 15 is generally a large-sized structure having a cylindrical shape and rotates about the rotational axis (i.e., Z-axis) under rotation driving of plural rotation drivers 23, which are in contact with the respective ring-shaped outer peripheral surfaces of both ends of the rotating gantry 15. Weight of the rotating gantry 15 is supported by foundations 21 via the rotation drivers 23.

The rotating gantry 15 rotates about the Z-axis in a state where the bed 24 fixed to the stationary system is disposed inside and the irradiation port 18 of the beam 19 is fixed to the body thereof.

The rotating gantry 15 is provided with many other controllers and structures such as a beam transport system 27 and a deflection electromagnet 28 of a beam in addition to the irradiation port 18 of the particle beam 19.

The particle beam 19 is formed by accelerating ions (i.e., heavy particles or proton ions generated by a non-illustrated ion source) with a linear accelerator and then making the accelerated ions incident on a non-illustrated circular accelerator to increase the energy of the ions to a preset value.

The beam transportation system 27 is provided so as to rotate integrally with the rotating gantry 15, and the particle beam outputted from the circular accelerator is made incident on the beam transportation system 27 from the extension line of the rotation axis Z of the beam transportation system 27.

The irradiation port 18 is inserted toward the inside of the rotating gantry 15 and rotates together with the rotating gantry 15 by ±180° around the bed 24.

The trajectory of the particle beam made incident on the beam transport system 27 is bent by the deflection electromagnet 28, and then the particle beam is irradiated onto a patient lying on the bed 24 in any direction of 0° to 360° from the irradiation port 18.

The bed 24 has a base fixed to the foundation of the building side, moves inside the rotating gantry 15, and positions a lesion area of a patient at the irradiation position of the particle beam 19.

After the particle beam 19 is irradiated towards the lesion area, the particle beam 19 decreases its speed by losing kinetic energy when passing through the patient's body, and suddenly stops when it falls to a certain speed by receiving a resistance which is approximately inversely proportional to the square of speed.

In the vicinity of the stop point of the particle beam 19, high energy called a Bragg peak is emitted. Since the bed 24 is positioned such that the release position of this Bragg peak coincides with the lesion area, only the tissues of the lesion area are killed and treatment with less damage of normal tissues is executed.

Figure 2B:
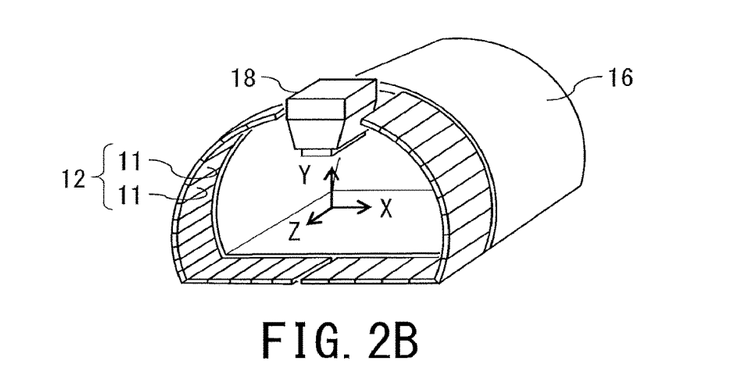
FIG. 2B is an overall perspective view of a moving floor and a tunnel structure of the particle beam treatment apparatus of each embodiment.

FIG. 2B is a schematic perspective view focusing on the moving floor 12 and the tunnel structure 16. Each of the plates 11 constituting the moving floor 12 is desired to have large flexural rigidity in the longitudinal direction and to be lightweight. The multiple plates 11 are joined to each other at the side edge portions thereof.

Since a part of the moving floor 12 is formed as an opening and the irradiation port 18 is fixed to the rotating gantry 15, the moving floor 12 can rotate in conjunction with (i.e., in synchronization with) the rotation of the rotating gantry 15 by causing the irradiation port 18 to pass through the opening.

As a form of the moving floor 12, in addition to the case of forming a single sheet in an annular shape, plural separate bodies and sheets of the respective separate bodies are formed in a annular shape in combination in some cases as described below in the second embodiment.

As shown in FIG. 1B, a first rail 13A and a second rail 13B are slidably engaged at one end and the opposite end of the moving floor 12, respectively. Each of the first rail 13A and the second rail 13B has a closed track composed of a circular arc and a straight line (FIG. 1A). Thus, the inner space of the moving floor 12 forms a tunnel shape surrounded by a flat horizontal floor and an arch-shaped ceiling, and the moving floor 12 can rotate about the rotation axis Z while keeping the tunnel shape stationary.

The moving floor 12 does not have to be wide in the direction of the rotation axis (i.e., Z-axis direction) because space of the treatment room is sufficiently secured due to the presence of the tunnel structure 16 described below. Hence, the moving floor 12 can be designed to be lightweight and have high mechanical rigidity, and thus the rotary motion of the moving floor 12 can be smoothly implemented while maintaining quietness.

The first rail 13A is supported at one end of a hollow body 53, the other end of which is connected to an opening of a vertical wall surface (stationary system) 60 of the foundation 21 fixing the bed 24.

The support of the first rail 13A from the foundation 21 is not limited to the illustrated method. For instance, the first rail 13A may be fixed to a non-illustrated supporting portion, which is rotatably provided with respect to the inner peripheral surface of the rotating gantry 15 and is supported by the vertical wall surface (stationary system) 60 of the foundation 21, in such a manner that the first rail 13A is indirectly supported by the stationary system.

The second rail 13B is fixed to the periphery of the tunnel structure 16 which substantially matches in sectional shape with the second rail 13B. The second rail 13B is disposed so as to face the first rail 13A with the irradiation port 18 interposed between the first and second rails 13A and 13B, and is engaged with the other end of the moving floor 12.

It is sufficient that the distance between the first and second rails 13A and 13B is slightly wider than the width of the irradiation port 18 interposed between them.

By reducing the length of the moving floor 12 in the direction of the rotation axis (Z-axis) in the range satisfying the above condition, both of weight reduction and improvement of mechanical rigidity can be achieved for the moving floor 12 rotating together with the rotating gantry 15.

The moving floor 12 can be omitted in some cases, e.g., in the case where the irradiation port 18 is further advanced and designed to have a smaller diameter and the gap between the hollow body 53 and the tunnel structure 16 can be reduced to such an extent that there is no obstacle to the comings and goings of technicians.

Although the tunnel structure 16 having the horizontal floor and the arch-shaped ceiling is illustrated, the tunnel structure 16 is satisfactory when it has at least a horizontal floor surface and internal space in which at least a part of the bed 24 is accommodated.

In the tunnel structure 16, a panel 51 is provided on the opposite side of the second rail 13B so as to close the opening. The panel 51 is supported by a rotation shaft 52 of the rotation support portion 57 which freely rotates. The position and orientation of the rotation shaft 52 match the rotation axis Z of the rotating gantry 15.

The rotation supporter 57 rotationally displaces the rotation shaft 52 which pivotally supports the tunnel structure 16 from a stand 56 fixed to the inner side surface 15a of the rotating gantry. As a result, the tunnel structure 16 is stationary with respect to the stationary system in such a manner that the flat floor surface always remains horizontal without depending on the rotational displacement of the rotating gantry 15.

In the stationary system, the rotation shaft 52 of the rotation supporter 57 is rotationally displaced in the direction opposite to the rotational direction of the rotating gantry 15. As a result of the rotation supporter 57 is fixed to the inner side surface 15a of the rotating gantry 15, thus the tunnel structure 16 is kept in the stationary state even when the irradiation port 18 rotates with respect to the stationary system.

Further, the rotation supporter 57 is provided with a support member 26 which supports its own weight in the vertical direction. One end of the support member 26 is fixed to the tunnel structure 16 or the panel 51, and the other end of the support member 26 frictionlessly contacts the inner side surface 15a of the rotating gantry 15 and rotates in the circumferential direction. It should be noted that the rotation shaft 52 of the rotation supporter 57 may be freely rotatable in addition to being driven and rotated by, e.g., a motor.

Although, a description has been given of the case where the rotation supporter 57 is composed of the rotation shaft 52 and the stand 56 in the present embodiment, the rotation supporter 57 is not limited to such an aspect. In the present embodiment, it is possible to adopt any rotation supporter 57 which can rotationally displace the tunnel structure 16 with respect to the inner side surface 15a of the rotating gantry 15.

According to the above-described tunnel structure 16, it is possible to form a treatment room having a flat horizontal floor surface and sufficient room size inside the rotating gantry 15 without depending on the rotational position of the irradiation port 18. This makes it possible to improve the workability of a technician who accesses a patient lying on the bed 24.

Since the majority of this wide treatment room can be provided by the tunnel structure 16, the length of the moving floor 12 in the direction of the rotation axis can be shortened to substantially the same length as that of the irradiation port 18 which is the minimum length required in terms of its function. As a result, the moving floor 12 can be fabricated with light weight and high rigidity or be omitted, and thus it is possible to provide a particle beam treatment apparatus in which robustness is enhanced and load of the rotation drive mechanism is reduced.

Second Embodiment

Next, a description will be given of the second embodiment of the present invention by referring to FIG. 3A, FIG. 3B, FIG. 4A, and FIG. 4B. In FIG. 3A, FIG. 3B, FIG. 4A, and FIG. 4B, the same reference signs are assigned to the same components as those in FIG. 1 in terms of configuration or function, and duplicate description is omitted.

The moving floor 12 applied to the particle beam treatment apparatus 10 of the second embodiment is divided at the position where the irradiation port 18 penetrates, and is composed of at least two separate bodies 17A and 17B. The separate body (i.e., the first plate group) 17A and the separate body (i.e., the second plate group) 17B respectively include traveling mechanisms 25A and 25B for independently traveling the respective closed tracks of the first and second rails 13A and 13B.

Specifically, a rack-and-pinion mechanism can be adopted as each of the traveling mechanisms 25A and 25B. In this case, a motor for rotating a small-diameter circular gear called a pinion is provided on the plate 11 arranged at the center of each of the separate bodies 17A and 17B. At least one of the first rail 13A and the second rail 13B is provided with a toothed rack. When rotational force is applied to the combination of the rack and the pinion, the rotational force is converted into linear force in the longitudinal direction of the rack, and the separate bodies 17A and 17B of the moving floor 12 move along the respective closed tracks of the first and second rails 13A and 13B.

The traveling mechanisms 25A and 25B are not limited to the rack-and-pinion mechanism and may be configured as any other mechanism as long as it can cause the separate bodies 17A and 17B to run independently of each other on the closed track of the first and second rails 13A and 13B.

The flat horizontal floor surface of the rotating moving floor 12 does not generate any gap and it is necessary to ensure the safety of the technicians coming and going. As can be seen by comparing FIG. 4A and FIG. 4B, the size of the opening of the moving floor 12 required to cause the irradiation port 18 to penetrate the moving floor 12 is different depending on the rotational position of the irradiation port 18. Thus, there is a circumstance that the side surface positions of the irradiation port 18 in contact with the respective edges of the separate bodies 17A and 17B change depending on the rotation position of the irradiation port 18.

Figure 4A:
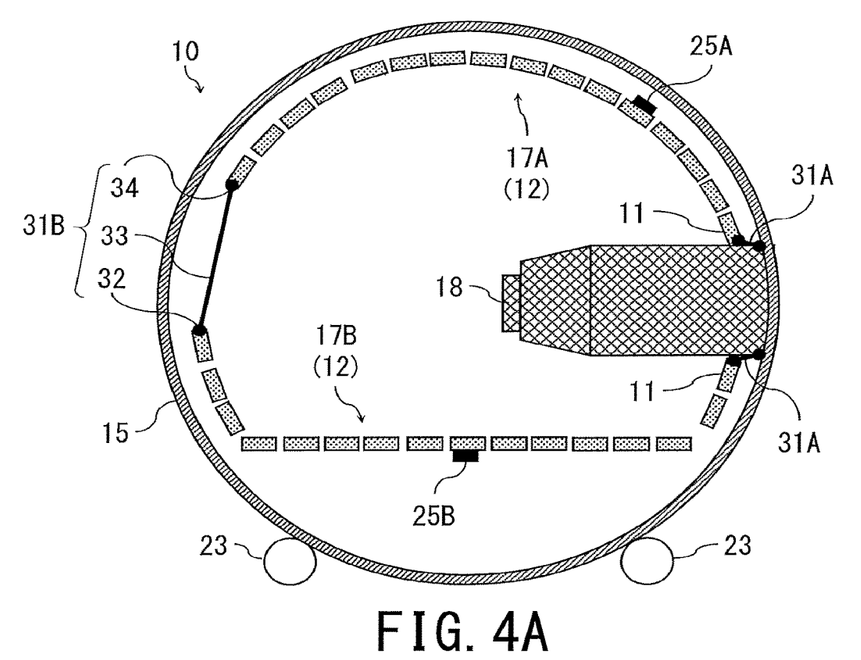
FIG. 4A and FIG. 4B are schematic diagrams illustrating the operation (i.e., movement) of the moving floor applied to the second embodiment.
Figure 4B:
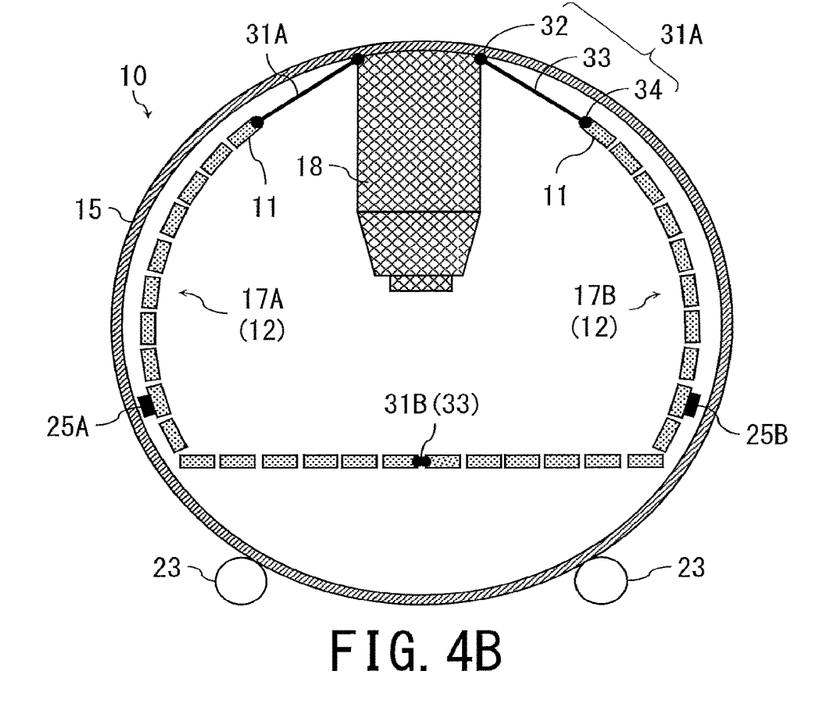

Hence, the traveling mechanisms 25A and 25B for moving the separate bodies 17A and 17B are controlled such that any gap does not generated on the flat horizontal floor surface when the respective edges of the separate bodies 17A and 17B are located on the flat horizontal floor surface. Specifically, the traveling mechanisms 25A and 25B are controlled such that the respective edges of the separate bodies 17A and 17B are brought into contact with the irradiation port 18 or brought into contact with each other when being located on the flat horizontal floor surface. As a result, anther opening is formed at the arch-shaped ceiling on the opposite side of the flat horizontal floor by the gap between the respective edges of the separate bodies 17A and 17B, and the size of this opening also changes depending on the rotational position of the irradiation port 18 and the opening is permissible.

Since a gap is formed between the irradiation port 18 and the separate body 17A, a shielding member 31A for shielding the formed gap is provided. Similarly, another shielding member 31A is provided for shielding the gap between the irradiation port 18 and the separate body 17B. Each of the shielding members 31A is provided with a roll 34 at the edge portion of the separate body 17A or 17B. Each shielding member 31A further include a sheet 33 wound around the roll 34, and the roll 34 is rotatably biased in the winding direction. The tip 32 of the wound sheet 33 is connected to the side surface of the irradiation port 18. It should be noted that the attachment positions of the roll 34 and the tip 32 of the sheet 33 may be reversed.

In this manner, the wound sheet 33 of each shielding member 31A expands and contracts depending on the size of the gap formed between the irradiation port 18 and each of the separate bodies 17A and 17B so as to shield the gap.

Further, a shielding member 31B is also provided between the respective edge portions of the separate bodies 17A and 17B in the state of being butted to each other. The shielding member 31B includes the roll 34 and the sheet 33 similarly to the shielding members 31A, and shields or fills the formed gap between the separate bodies 17A and 17B depending on the size of the gap.

Specifically, on the side opposite to the irradiation port 18, the roll 34 of the shielding member 31B is provided on one of the edge portions of the two separate bodies 17A and 17B which are in close proximity to each other while the tip 32 of the sheet 33 of the shielding member 31B is connected to the other of the edge portions of the two separate bodies 17A and 17B.

In the second embodiment, the shielding members 31A and 31B are not indispensable components. In other words, the shielding members 31A and 31B may be omitted when it is not important that the inner side surface 15a of the rotating gantry 15 is exposed from the opening of the moving floor 12 formed on the arch side.

Figure 3A:
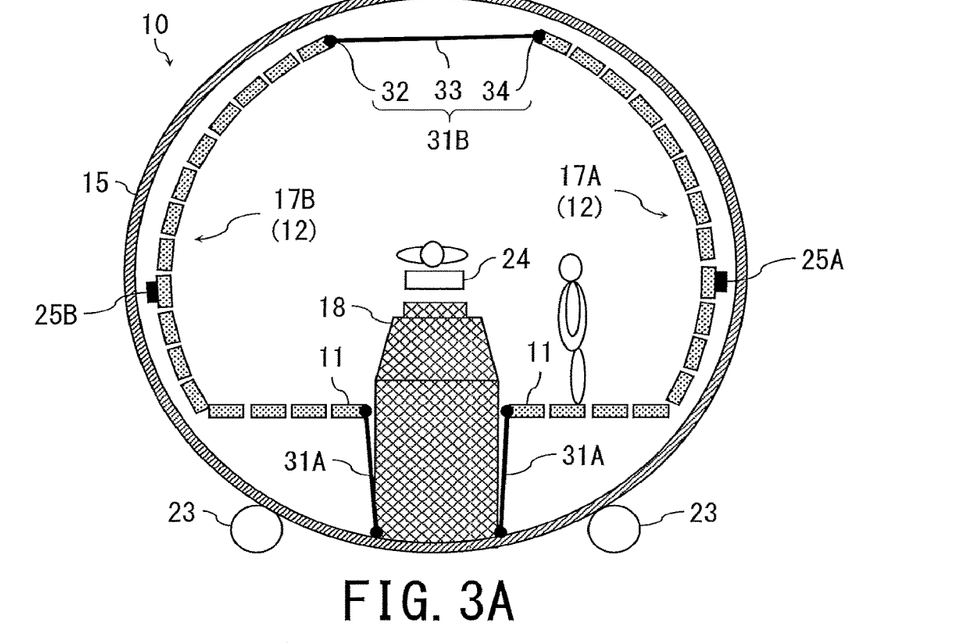
FIG. 3A and FIG. 3B are schematic diagrams illustrating an operation (i.e., movement) of the moving floor applied to the second embodiment.

Consider a case where the rotation angle of the rotating gantry 15 is set to +180° and the irradiation port 18 is positioned directly under the bed 24 as shown in FIG. 3A. In this case, by bringing the irradiation port 18 into contact with the respective edge portions of the separate bodies 17A and 17B, the horizontal flat floor surface of the moving floor 12 is formed without forming openings on both sides of the irradiation port 18.

Also in this case, each of the shielding members 31A provided on both sides of the irradiation port 18 becomes the state in which the sheet 33 extends between the base portion of the irradiation port 18 and the edge portion of the separate body 17A or 17B.

Also in this case, the shielding member 31B at the butting position of the separate bodies 17A and 17B on the arch side becomes the state in which the sheet 33 extends in order to shield the formed gap.

Figure 3B:
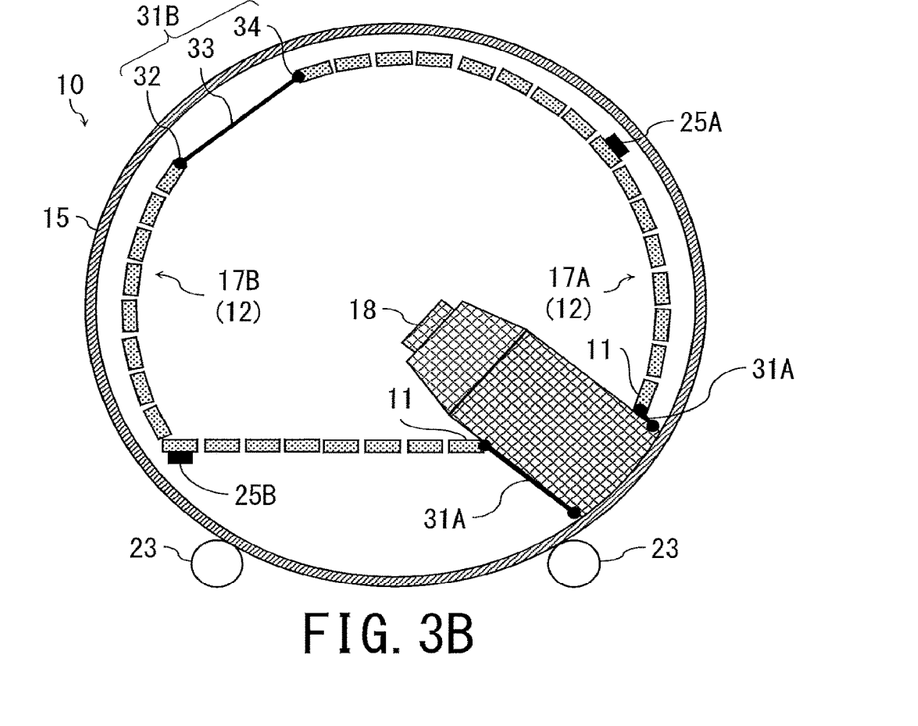

Next, consider a case where the rotation angle of the rotating gantry 15 is set to +135° and the irradiation port 18 is positioned obliquely below the bed 24 as shown in FIG. 3B. In this case, the edge of the separate body 17A on the right side of the FIG. 3B reaches the base of the irradiation port 18. Also in this case, by bringing the respective edge portions of the separate bodies 17A and 17B into contact with the irradiation port 18, the horizontal flat floor surface of the moving floor 12 is formed without forming an opening.

Further, consider a case where the rotation angle of the rotating gantry 15 is set to +90° and the irradiation port 18 is positioned right beside the bed 24 as shown in FIG. 4A. In this case, the respective edges of both separate bodies 17A and 17B reach the base of the irradiation port 18. Also in this case, by bringing the respective edge portions of the separate bodies 17A and 17B into contact with the irradiation port 18, the horizontal flat floor surface of the moving floor 12 is formed without forming an opening.

Under the state where the horizontal flat floor surface is formed as shown in FIG. 4A, each of the shielding members 31A provided on the side of the irradiation port 18 becomes the state in which the sheet 33 contracts between the base portion of the irradiation port 18 and the edge portion of the separate body 17A or 17B. Also under this state, the shielding member 31B at the butting position of the separate bodies 17A and 17B on the opposite side becomes the state in which the sheet 33 extends so as to shield the formed gap.

Further, consider a case where the rotation angle of the rotating gantry 15 is set to 0° and the irradiation port 18 is positioned directly above the bed 24 as shown in FIG. 4B. In this case, by bringing the respective edge portions of both separate bodies 17A and 17B into contact with each other on the horizontal floor surface, the horizontal flat floor surface of the moving floor 12 is formed without forming an opening.

Also in this case, the shielding member 31B positioned on the horizontal flat floor surface becomes the state in which the sheet 33 is contracted, and each of the shielding members 31A provided on both sides of the irradiation port 18 on the arch side becomes the state in which the sheet 33 is extended between the base portion of the irradiation port 18 and the edge portion of the separate body 17A or 17B so as to shield the generated gap.

The above-described positional relationship between the irradiation port 18 and the separate bodies 17A and 17B and the expansion/contraction relationship of the shielding members 31A and 31B are given as some possible aspects, and the embodiments of the present invention are not limited to such aspects. Thus, these relationships are appropriately changed depending on the arcuate orbit (i.e., track) of the first and second rails 13A and 13B, the length of the linear track, and/or the size of the irradiation port 18. Although a description has been given of a case where the rotating gantry 15 rotates in the range of +180° to 0°, the rotating gantry 15 also rotates in the range of 0° to −180°.

Each of the rotating gantry 15 and the irradiation port 18 has a mirror symmetrical shape. Thus, even when the rotating gantry 15 rotates in the range of 0° to −180°, motions of the separate bodies 17A and 17B are appropriately controlled such that any opening is not formed on the horizontal floor surface of the moving floor 12.

In the particle beam treatment apparatus 10 of the second embodiment, it is an essential requirement that the moving floor 12 is composed of the separate bodies 17A and 17B and the separate bodies 17A and 17B are provided with the respective traveling mechanisms 25A and 25B. Thus, the particle beam treatment apparatus 10 without the tunnel structure 16 and/or the shielding members 31A and 31B may also be possible as one aspect of the second embodiment.

Third Embodiment

Figure 5A:
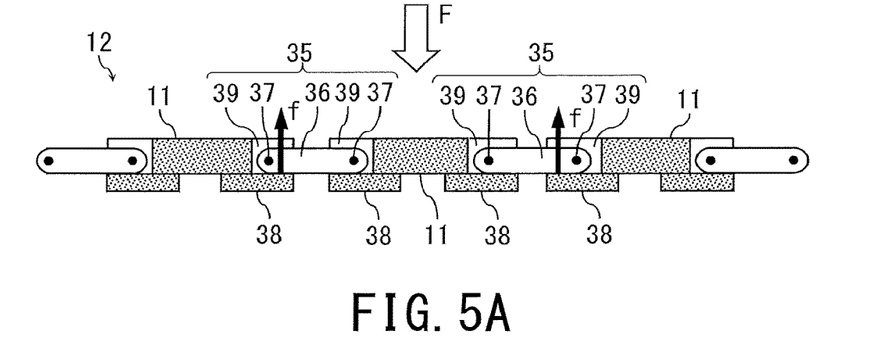
FIG. 5A is a side view illustrating a connecting portion of plates of the moving floor applied to the third embodiment.
Figure 5B:
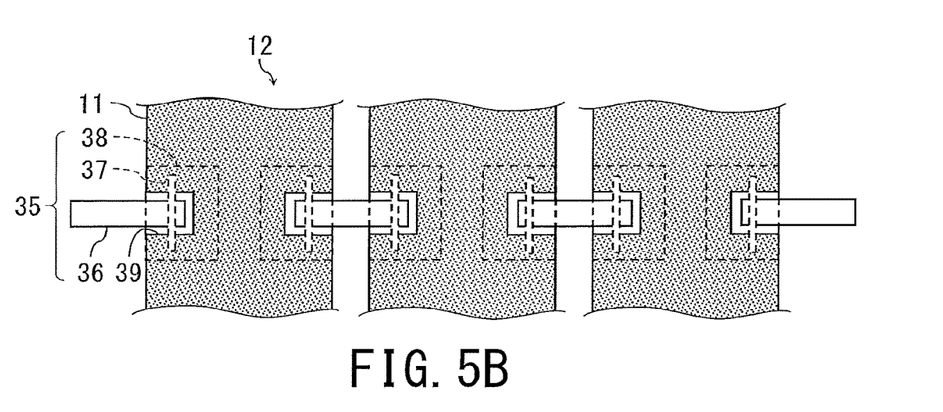
FIG. 5B is a top view illustrating the connecting portion of the plates of the moving floor.
Figure 5C:
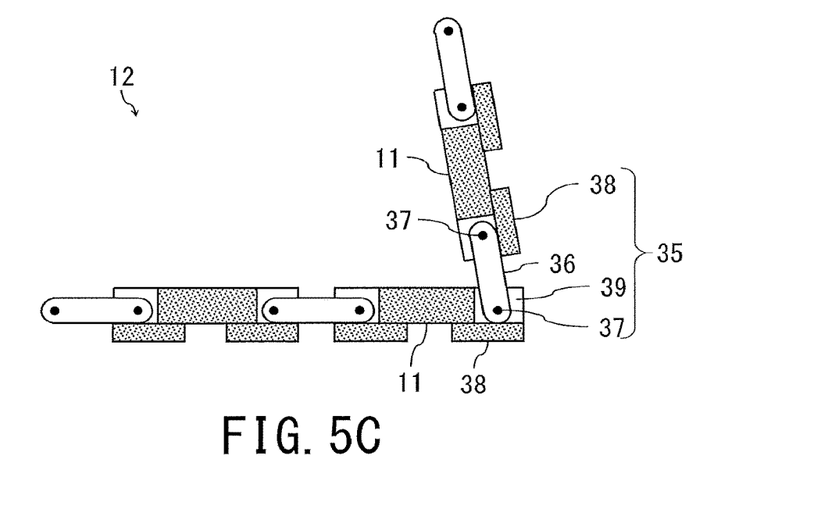
FIG. 5C is a side view illustrating the connecting portion of the plates of the moving floor in the state of being bent.

Next, a description will be given of the third embodiment of the present invention by referring to FIG. 5A, FIG. 5B, and FIG. 5C. FIG. 5A to FIG. 5C are enlarged views of each connecting portion 35 of the plates 11 of the moving floor 12 applied to the third embodiment. In FIG. 5A to FIG. 5C, the same reference signs are assigned to the same components as those in FIG. 1A and FIG. 1B in terms of configuration or function, and duplicate description is omitted.

As shown in FIG. 5A to FIG. 5C, each connecting portion 35 includes a joint 36, a pair of shafts 37, and a restricting member 38. The joint 36 links two adjacent plates 11 together. The pair of shafts 37 rotatably support both ends of the joint 36 at both notches 39 provided at both edges of each plate 11. Then the each restricting member 38 regulates the rotation of each joint 36 so as to allowing bending of the plates 11 towards the bed while restricting bending of the plates 11 to the opposite side.

The connecting portion 35 configured as described above is provided at each gap between adjacent two plates 11. Thus, when the stress F is applied to the plate 11 shown in FIG. 5A, the two restricting members 38 provided on both sides of this plate 11 give the reaction force f to prevent the joint 36 from rotate in the direction that the plates 11 about to displace downward with respect to the adjacent two plates 11 on both sides. As a result, the moving floor 12 is given high mechanical rigidity so that the horizontal floor surface does not deform to a large extent even when a technician or a patient rides thereon.

At the corner of the tunnel shape of the moving floor 12 as shown in FIG. 5C, it is possible for the plates 11 adjacent to each other to bend as a whole with the shaft 37 as the center. Similarly, a curved surface can be formed also in the tunnel-shaped arch portion without stress.

Although a block member provided on the lower side of the notch 39 of each plate 11 is illustrated as each restricting member 38, each restricting member 38 is not particularly limited to such an aspect. Any structure that prevents the joint 36 for the plate 11 from bending towards the outside of the moving floor 12 can be used as the restricting member 38.

In the particle beam treatment apparatus 10 of the third embodiment, it is required that the joints 36 of the moving floor 12 are allowed to bend the plates 11 as a whole to the bed side and the bending to the opposite side is restricted. Thus, the particle beam treatment apparatus 10 unequipped with the tunnel structure 16 may also be possible as one aspect of the third embodiment. Additionally, the particle beam treatment apparatus 10 in which the moving floor 12 is not composed of the separate bodies 17A and 17B may also be possible as another aspect of the third embodiment. Further, the particle beam treatment apparatus 10 in which the moving floor 12 is unequipped with the shielding members 31A and 31B may also be possible as still another aspect of the third embodiment.

According to the particle beam treatment apparatus of at least one of the above-described embodiments, a treatment space is widely formed by providing the tunnel structure, and it is possible to improve general versatility and robustness by shielding the gap of the moving floor and/or improving its mechanical rigidity.

Some embodiments of the present invention have been described above. These embodiments have been presented as examples. There is no intention to limit the scope of the invention. These embodiments can also be implemented in other various modes, and variously omitted, replaced, changed, and combined without departing from the gist of the invention. The embodiments and their variations are encompassed by the scope and gist of the invention. Likewise, these embodiments and variations are encompassed by the invention described in the claims and its range of equivalence.

What is claimed is:

1. A particle beam treatment apparatus comprising:
   a rotating gantry configured to axially rotate in a state Where a bed fixed to a stationary system is disposed inside the rotating gantry and an irradiation port of a beam is fixed to a body of the rotating gantry;
   a tunnel structure configured to have at least a horizontal floor surface and have an internal space in which at least a part of the bed is accommodated;
   a rotation supporter configured to cause the tunnel structure to be stationary in the stationary system independently of axis rotation of the rotating gantry by rotationally displacing the tunnel structure with respect to an inner side surface of the rotating gantry;
   a moving floor configured to be formed by bendably joining a plurality of plates to each other in an annular shape such that the internal space is continuous from the tunnel structure, and rotate together with the rotating gantry in a state where the irradiation port penetrates the moving floor;
   wherein one end of the moving floor is engaged with a first rail, which is supported by the stationary system and includes a closed track substantially matching in vertical cross-sectional shape with the tunnel structure; and
   another end of the moving floor is engaged with a second rail fixed to the tunnel structure, the second rail is disposed to face the first rail such that the irradiation port is interposed between the first rail and the second rail.

2. The particle beam treatment apparatus according to claim 1,
   wherein the moving floor is composed of at least two separate bodies, respective edges of which divide connection of the plurality of plates at a portion which the irradiation port penetrates; and
   the at least two separate bodies includes traveling mechanisms for independently traveling the respective closed tracks of the first rail and the second rail.

3. The particle beam treatment apparatus according to claim 2, further comprising a shielding member which is equipped with a roll and a sheet, is provided between the irradiation port and an edge portion of each of two separate bodies interposing the irradiation port, and is configured to shield a gap formed between the irradiation port and the edge portion;
   wherein a tip of the sheet is connected to one of the irradiation port and the edgy portion while the roll is provided at another of the irradiation port and the edge portion; and
   one side of the sheet being opposite to the tip is wound around the roll in such a manner that the roll is rotatable biased in a winding direction of the sheet.

4. The particle beam treatment apparatus according to claim 3,
   wherein both the tip and the roll of the sheet are connected to the edge portion of each of the two separate bodies to shield a gap formed between the each edge portion of the two separate bodies.

5. The particle beam treatment apparatus according to claim 1, the moving floor further comprising:
   a joint configured to link two of the plurality of plates adjacent to each other;
   a pair of shafts configured to rotatably support both ends of the joint at respective notches provided at both edges of the plates; and
   a restricting member configured to regulate the rotation of the joint to allow bending of the plurality of plates towards the bed and to restrict bending of the plurality of plates towards a side opposite to the bed.

* * * * *